(12) United States Patent
Shimizu et al.

(10) Patent No.: US 7,157,608 B2
(45) Date of Patent: Jan. 2, 2007

(54) PROCESS FOR PRODUCING ALLYL ETHER

(75) Inventors: Yasumi Shimizu, Osaka (JP); Kaoru Nakao, Osaka (JP); Tohru Matsutomi, Osaka (JP)

(73) Assignee: Daiso Co., Ltd., Osaka (JP)

( * ) Notice: Subject to any disclaimer, the term of this patent is extended or adjusted under 35 U.S.C. 154(b) by 92 days.

(21) Appl. No.: 10/516,026

(22) PCT Filed: Jun. 7, 2002

(86) PCT No.: PCT/JP02/05638

§ 371 (c)(1),
(2), (4) Date: Nov. 29, 2004

(87) PCT Pub. No.: WO03/104177

PCT Pub. Date: Dec. 18, 2003

(65) Prior Publication Data

US 2005/0215830 A1 Sep. 29, 2005

(51) Int. Cl.
*C07C 41/01* (2006.01)
(52) U.S. Cl. ....................... 568/673; 568/675
(58) Field of Classification Search .......... 568/673, 568/675
See application file for complete search history.

(56) References Cited

U.S. PATENT DOCUMENTS 2,585,035 A * 2/1952 Roach et al. .......... 526/238.23
4,142,042 A 2/1979 Goble .................. 568/616
4,433,179 A 2/1984 Lohse et al.

FOREIGN PATENT DOCUMENTS

| JP | 57-81418 | 5/1982 |
| JP | 62-223141 | 10/1987 |
| JP | 3-80141 | 12/1991 |
| JP | 4-4303 | 1/1992 |
| JP | 2001-122922 | 5/2001 |

OTHER PUBLICATIONS

P. L. Nichols et al., "Allyl Ethers of Carbohydrates. II. Preparation and Polymerization of Polyallyl Ethers", Journal of the American Chemical Society, vol. 67, pp. 46-49, Jan. 1945.

* cited by examiner

*Primary Examiner*—Rosalynd Keys
(74) *Attorney, Agent, or Firm*—Wenderoth, Lind & Ponack, L.L.P.

(57) ABSTRACT

In the production of allyl ethers of polyol by reacting a straight-chain polyol compound with an allyl halide in the presence of an alkali metal hydroxide, wherein the straight-chain polyol compound has carbon atoms each having one hydroxyl group, the reaction between the straight-chain polyol compound and the allyl halide is proceeded in the presence of water having the amount dissolving the straight-chain polyol compound at a reaction temperature, then 14% by mol, based on total molar amount of a hydroxyl group contained in the straight-chain polyol compound, of the allyl halide is added to a reaction system before at least part of water is released out of the reaction system.

5 Claims, No Drawings

PROCESS FOR PRODUCING ALLYL ETHER

TECHNICAL FIELD

The present invention relates to a method of industrially and practically producing allyl ethers of straight-chain polyol in a high yield.

RELATED ART

Hitherto, some documents propose a technology of allyl-etherifying a polyol. Examples of a document disclosing the method of allyl-etherifying a polyol having a non-straight-chain structure (a branched-chain polyol) are as follows. JP-B-04-4303 discloses that an allyl alcohol is added as an accelerating agent when allyl ethers of pentaerythritol are prepared. In addition, JP-B-03-80141 discloses a method of adjusting the total amount of water added to a reaction system when allyl ethers of trimethylolpropane are prepared.

As to a polyol having a straight-chain structure, JP-A-57-81418 discloses a method of using a tetrabutyl ammonium acidic sulfate salt as a phase transfer catalyst. However, this method has many industrial disadvantages in view of the defect that a step of removing a catalyst is necessary, and the defect that it is necessary to adopt a measure for avoiding the incorporation of a catalyst or a residue thereof into a product.

Since the straight-chain polyol has extremely large hydrophilicity, a solvent for largely dissolving the straight-chain polyol in a practical level is substantially limited to water. Even if it is intended that the straight-chain polyol is reacted with an allyl halide and an alkali metal hydroxide under the reaction conditions that water is completely absent, the reaction hardly proceeds or does not proceed at all. Thus, the reaction is proceeded by dissolving the straight-chain polyol in water, but the contact between the straight-chain polyol and the allyl halide is poor at the beginning of the reaction so that the reaction hardly proceeds. Even if an accelerating agent such as allyl alcohol is used, the reaction of the straight-chain polyol hardly proceeds in comparison with the branched-chain polyol such as pentaerythritol so that it was difficult to produce the allyl ether of polyol from the straight-chain polyol at the industrially practical level.

Although the presence of water is necessary at the beginning of the reaction, water causes the decrease of a reaction rate and the generation of a hydrolysis reaction of the allyl halide so that the yield is decreased. Thus, JP-B-4-4303 discloses a method of distilling off water in a reaction system at the stage when the reaction rate becomes large, in the preparation of allyl ether of pentaerythritol from pentaerythritol and allyl chloride. However, this method is successful for pentaerythritol which a branched-chain polyol, but, when used for a straight-chain polyol, this method was insufficient in the yield, the complicated post-treatment due to insolubility of the residual straight-chain polyol, the control of distribution of allylation number and average allylation number of the product, and the period of time for whole reaction.

SUMMARY OF THE INVENTION

The present inventors intensively studied a method of preparing an allyl ether of polyol from a straight-chain polyol compound, which method has the excellent productivity at an industrially practical level, the high conversion of raw materials and the high yield of the product.

The present inventors carefully observed the step of reacting allyl chloride by only reflux without discharging water; discovered that, when at least 14% by mol, based on 1 mol of a hydroxyl group of the straight-chain polyol compound, of the allyl chloride is added, a sufficient amount of an oil layer is rapidly formed by the hydrophobization caused by allylation and the raw material, sorbitol is sufficiently decreased at this time, the raw material substantially disappears, even if the process is shifted to a dehydration step.

The present invention provides a method of producing allyl ethers of polyol by reacting a straight-chain polyol compound with an allyl halide in the presence of an alkali metal hydroxide, wherein the straight-chain polyol compound has carbon atoms each having one hydroxyl group, and is represented by the general formula (1):

$$HOCH_2[CH(OH)]_nCH_2OH \qquad (1)$$

wherein n is an integer of from 2 to 6, characterized in that the reaction between the straight-chain polyol compound and the allyl halide is proceeded in the presence of water having the amount dissolving the straight-chain polyol compound at a reaction temperature, then 14% by mol, based on total molar amount of a hydroxyl group contained in the straight-chain polyol compound, of the allyl halide is added to a reaction system before the discharge of water out of the reaction system is initiated.

The transfer to the dehydration step at an earlier stage is usually advantageous to prevent the reaction rate decrease caused by lower concentration of alkaline hydroxide and the increase of side reactions. However, if the process shifts to the dehydration step before at least 14% by mol of allyl chloride is added and reacted, sorbitol having high water-solubility, which remains at that time, tends to remain unreacted.

DETAILED EXPLANATION OF THE INVENTION

The method of the present invention is generally conducted by adding the allyl halide to a reaction vessel (or a reaction zone) which contains a whole amount of the straight-chain polyol compound.

In one embodiment of the present invention, (A) the straight-chain polyol compound, the alkali metal hydroxide and water having an amount dissolving the straight-chain polyol compound at a reaction temperature are added into the reaction vessel, (B) at least part of the allyl halide is added to the reaction vessel so that the reaction between the straight-chain polyol compound and the allyl halide is initiated, and then (C) after at least 14% by mol, based on total molar amount of the hydroxyl group contained in the straight-chain polyol compound, of the allyl halide is added to the reaction vessel, the release of water out of the reaction vessel is initiated.

In the formula (1) of the straight-chain polyol compound, the number of n may be particularly from 2 to 4. Examples of the straight-chain polyol compound are a straight-chain sugar alcohol, particularly erythritol, xylitol and sorbitol.

Examples of the allyl halide are allyl chloride and allyl bromide.

Examples of the alkali metal hydroxide are lithium hydroxide, sodium hydroxide and potassium hydroxide.

In the present invention, the allyletherification reaction of the straight-chain polyol compound is preferably conducted by adding the allyl halide to the reaction system (that is, reaction vessel) containing whole amount of the straight-chain polyol compound to be reacted. The addition of the allyl halide may be conducted continuously or intermittently. For example, the allyl halide may be dropwise added, or whole amount of the allyl halide may be divided into several (for example, 3 to 20) small portions and said small portions may be added one after another.

In the present invention, water is present in the amount for dissolving the straight-chain polyol compound at the reaction temperature, during a period of time between the initiation of allyletherification reaction and the beginning of discharge of water out of the reaction system. This does not exclude the state that at least part or whole of the used allyl halide is present at the initiation of allyletherification reaction.

After the initiation of the reaction, water may be added so that whole of the straight-chain polyol compound is dissolved at the reaction temperature. Water is preferably present before the initiation of the allyletherification reaction in such amount that whole of the straight-chain polyol compound is dissolved at the reaction temperature. Water may be appropriately added during the proceeding of the reaction.

The amount of water present in the reaction system may be at least 20% by mol, for example 20 to 250% by mol, particularly 100 to 220% mol, especially 140 to 180% by mol, based on mol of total hydroxyl groups contained in the straight-chain polyol compound. When the amount of water is sufficient for dissolving the straight-chain polyol compound, the speed of the allyletherification reaction is large.

The present invention does not limit the amount of the alkali metal hydroxide introduced into the reaction system until the time at which the discharge of water out of the reaction system is initiated. Said amount of the alkali metal hydroxide may be from 26 to 100% by mol, for example 28 to 75% by mol, particularly 28 to 60% by mol, more preferably from 30 to 45% by mol, particularly preferably from 30 to 42% by mol, based on mol of total hydroxyl groups contained in the straight-chain polyol compound. The alkali metal hydroxide may be charged in the necessary amount before the reaction or may be appropriately added during the reaction proceeding. The added alkali metal hydroxide may be in the form of a solid or an aqueous solution. Generally, the alkali metal hydroxide is added in the form of the aqueous solution in which the alkali metal hydroxide is dissolved in water.

Water is not discharged out of the reaction system until at least 14% by mol, based on mol of total hydroxyl groups contained in the straight-chain polyol compound, of the allyl halide is introduced into the reaction system. After at least 14% by mol, preferably at least 16% by mol, more preferably at least 18% by mol, particularly at least 20% by mol of the allyl halide is into the reaction system, the discharge of water is initiated. At the time when the desired amount of the allyl halide is introduced into the reaction system, an oil layer in the sufficient amount for dissolving the straight-chain polyol compound is rapidly formed by the hydrophobization caused by allylation and the amount of the raw material, the straight-chain polyol compound is sufficiently decreased. Therefore, even if the dehydration is conducted, the reaction of the straight-chain polyol compound sufficiently proceeds.

If the discharge of water is initiated earlier (i.e., before the given amount of the allyl halide is introduced into the reaction system), the straight-chain polyol compound having no allylation remains in a large amount in the final reaction product so that by-products are present in a large amount and a product distribution is broad. Even if a refinement procedure such as washing and distillation is conducted to give a sharp product distribution, the conversion of raw materials is low at the reaction completion, the decrease of yield cannot be prevented, and earlier initiation of water discharge is economically disadvantageous.

The discharge of water out of the reaction system can be conducted by, for example, distillation.

In the present invention, the temperature of the allyletherification reaction is, for example, from 70° C. to 130° C. The time of the allyletherification reaction is, for example, from 8 hours to 24 hours. A period of time between the initiation of the allyletherification reaction and the initiation of the discharge of water is, for example, from 2 hours to 14 hours.

The allyl ethers of polyol obtained by the method of the present invention have at least two allyl groups. The allyl ethers generally have at least one hydroxyl group and at least two allyl groups. The number of hydroxyl groups is at least one, for example at least two, and specific example of the number of hydroxyl groups is from 1 to 4. The number of allyl groups is at least 2, for example at least 3, particularly from 3 to 5. In the case of the mixture of hydroxypolyallyl ethers, an average number of hydroxyl groups is at least 0.5, for example at least 1.0, particularly at least 1.5, and an average number of allyl groups is at least 2.0, for example at least 2.5, particularly at least 3.0. The number of allyl groups (including the average number thereof is determined by gas chromatography and NMR (particularly, $^1$H NMR).

The allyl ethers of polyol can be used as a crosslinking agent and the like.

PREFERRED EMBODIMENTS OF THE INVENTION

Hereinafter, the present invention is illustrated with reference to the following Examples and Comparative Examples.

EXAMPLE 1

859 g of a 70% aqueous solution of D-sorbitol, 583 g of a 48% of an aqueous solution of sodium hydroxide and 60 mL of allyl alcohol were charged into a 2,000 mL reactor equipped with an agitator, a reflex condenser, a thermometer and two dropping funnels, and the mixture was heated. At the time when the temperature became 90° C., the dropwise addition of allyl chloride from one dropping funnel was initiated. The amount of the dropwise addition of allyl chloride was controlled to adjust the reaction temperature to at least 70° C. while whole amount of the reflux liquid is returned to the reactor.

The addition of 200 g of allyl chloride was completed at 3.7 hours after the reaction initiation, the addition of allyl chloride was continued. The time required for the addition of 300 g of allyl chloride was 5.5 hours after the reaction initiation. At this time (at the time when 20% by mol, based on total mol of hydroxyl group contained in D-sorbitol, of allyl halide was added), a water metering reservoir was attached between the reflux condenser and the reactor so that the reflux liquid is separated to return the oil layer alone to the reactor. The time required for the addition of totally 459 g of allyl chloride was 8 hours after the reaction initiation. At this time, the dropwise addition of 333 g of a 48% aqueous solution of sodium hydroxide from a different dropping funnel was initiated. The time required for the addition of totally 842 g of allyl chloride was 11 hours after the reaction initiation. The temperature was in the range between 70° C. and 90° C. After matured for 1 hour, the reaction mixture was cooled.

The reaction product was a slurry which was a mixture of a yellowish brown oil and solid particles, and a water layer was absent in the reaction product. After distilled off low-boiling-point materials, the oil was analyzed by gas chromatography and $^1$H NMR. The composition (% by weight) was as follows. D-sorbitol: 0.0%, D-sorbitol monoallyl ether: 0.4%, diallyl ether: 11.3%, triallyl ether: 35.4%, tetraallyl ether: 40.5%, pentaallyl ether: 12.9%, hexaallyl ether: 0.2%. An average molar number of allyl groups added to one molecule of D-sorbitol was 3.5.

Comparative Example 1

859 g of a 70% aqueous solution of D-sorbitol, 417 g of a 48% of an aqueous solution of sodium hydroxide and 60 mL of allyl alcohol were charged into a 2,000 mL reactor equipped with an agitator, a reflex condenser, a thermometer and two dropping funnels, and the mixture was heated. At the time when the temperature-became 90° C., the dropwise addition of allyl chloride was initiated. The amount of the dropwise addition of allyl chloride was controlled to adjust the reaction temperature to at least 70° C. while whole amount of the reflux liquid is returned to the reactor. The addition of 200 g of allyl chloride was completed at 7 hours after the reaction initiation. At this time (at the time when 13% by mol, based on total mol of hydroxyl group contained in D-sorbitol, of allyl halide was added), a water metering reservoir was attached between the reflux condenser and the reactor so that the reflux liquid is separated to return the oil layer alone to the reactor. The time required for the addition of totally 306 g of allyl chloride was 10.5 hours after the reaction initiation. At this time, the dropwise addition of 500 g of a 48% aqueous solution of sodium hydroxide from a different dropping funnel was initiated. The time required for the addition of totally 842 g of allyl chloride was 14.5 hours after the reaction initiation. The temperature was in the range between 70° C. and 90° C. After matured for 1 hour, the reaction mixture was cooled.

The reaction product was a slurry which was a mixture of a yellowish brown oil and solid particles, and a water layer was absent in the reaction product. After distilled off low-boiling-point materials, the oil was analyzed by gas chromatography and $^1$H NMR. The composition (% by weight) was as follows. D-sorbitol: 18.3%, D-sorbitol monoallyl ether: 0.2%, diallyl ether: 7.3%, triallyl ether: 25.5%, tetraallyl ether: 34.9%, pentaallyl ether: 13.6%, hexaallyl ether: 0.2%. An average molar number of allyl groups added to one molecule of D-sorbitol was 3.0.

Effect of the Invention

The present invention provides a method of preparing an allyl ether of a straight-chain polyol, which method has the excellent practical productivity at an industrial level and the high conversion of raw materials. In the present invention, the following advantageous effects are achieved:

1) The yield is increased.
2) The complication of post-steps caused by insolubility of the remaining straight-chain polyol compounds is eliminated.
3) The distribution of allylation number and the average allylation number can be excellently controlled.
4) The total production time can be shortened.

The invention claimed is:

1. A method of producing an allyl ether of polyol comprising
   reacting a straight-chain polyol compound with an allyl halide in the presence of an alkali metal hydroxide and water in a reaction system,
   wherein the straight-chain polyol compound has carbon atoms each having one hydroxyl group, and the straight chain polyol compound is represented by the general formula (1):

$$HOCH_2[CH(OH)]_nCH_2OH \qquad (1)$$

wherein n is an integer of from 2 to 6,
   wherein the water is present in an amount to dissolve the straight-chain polyol compound at a reaction temperature,
   initiating a discharge of water out of the reaction system during the reaction of the straight-chain polyol compound with the allyl halide, after at least 14% by mol or more of the allyl halide has been added to the reaction system, based on total molar amount of the hydroxyl group of the straight-chain polyol compound.

2. The method according to claim 1, wherein
   (A) the straight-chain polyol compound, the alkali metal hydroxide and the water are added into a reaction vessel, wherein
   (B) the reaction between the allyl halide and the straight-chain polyol compound is initiated when at least part of the allyl halide is added to the reaction vessel, and wherein
   (C) after at least 14% by mol of the allyl halide has been added to the reaction vessel, based on total molar amount of the hydroxyl group contained in the straight-chain polyol compound, the release of water out of the reaction vessel is initiated.

3. The method according to claim 1, wherein the allyl halide is allyl chloride, and the alkali metal hydroxide is sodium hydroxide.

4. The method according to claim 1, wherein the straight-chain polyol compound is selected from the group consisting of erythritol, xylitol and D-sorbitol.

5. The method according to claim 1, wherein the straight-chain polyol compound is D-sorbitol.

* * * * *